United States Patent [19]

Larock et al.

[11] Patent Number: 4,664,765

[45] Date of Patent: May 12, 1987

[54] PHOTOCHEMICAL SYNTHESIS OF ALLENIC AND PROPARGYLIC ORGANOMERCURIC HALIDES

[75] Inventors: Richard C. Larock, Ames, Iowa; Min-Shine Chow, Hsinchu, Taiwan

[73] Assignee: Iowa State University Research Foundation, Inc., Ames, Iowa

[21] Appl. No.: 768,636

[22] Filed: Aug. 23, 1985

[51] Int. Cl.$^4$ ............................................. B01J 19/12
[52] U.S. Cl. ........................... 204/157.75; 204/157.98; 204/157.99; 204/158.12
[58] Field of Search .................... 204/157.75, 157.98, 204/157.99, 158.12

[56] References Cited

U.S. PATENT DOCUMENTS

| | | | |
|---|---|---|---|
| 2,090,927 | 8/1937 | Andersen | 260/431 |
| 2,675,400 | 4/1954 | Howard | 556/126 |
| 2,790,816 | 4/1957 | Werner et al. | 536/121 |
| 2,790,817 | 4/1957 | Werner et al. | 556/122 |
| 2,883,409 | 4/1959 | Flenner | 556/122 |
| 2,914,451 | 11/1959 | Baldoni et al. | 204/157.75 |
| 2,986,566 | 5/1961 | Schutt | 548/533 |
| 3,641,061 | 2/1972 | Napler et al. | 549/209 |

OTHER PUBLICATIONS

M. Gaudemar, *Bul. Soc. Chim. France*, 1962, 974.
L. Henry, *Ber.Dt.Chem.Ges.*, 1884, 17, 1132.

*Primary Examiner*—Howard S. Williams
*Attorney, Agent, or Firm*—Zarley, McKee, Thomte, Voorhees & Sease

[57] ABSTRACT

Propargylic halides, preferably the bromide and iodide, react with metallic mercury in a finely divided state, in the presence of sunlight to form the corresponding allenic or propargylic organomercuric halides in high yield.

4 Claims, No Drawings

PHOTOCHEMICAL SYNTHESIS OF ALLENIC AND PROPARGYLIC ORGANOMERCURIC HALIDES

BACKGROUND OF THE INVENTION

Propargylic and allenic organometallics are of great interest, because they process tremendous potential in synthetic organic chemistry. For a review of these types of compounds and their many uses in synthetic organic chemistry, see J.-L. Moreau in "The Chemistry of Ketenes, Allenes and Related Compounds", ed. S. Patai, J. Wiley, New York, 1980, pp. 363–414, which is incorporated by reference. For other similar references see H. Hiemstra and W. Nico Speckamp, *Tetrahedron Lett.*, 1983, 23, 1407; N. R. Pearson, G. Hahn and G. Zweifel, *J. Org. Chem.*, 1982, 47, 3364; C. Huynh and G. Linstrumelle, *J. Chem. Soc., Chem. Commun.*, 1983, 1133; M. Ishiguro, N. Ikeda and H. Yamamoto, *J. Org. Chem.*, 1982, 47, 2225; C. J. Elsevier, H. Kleijn, K. Ruitenberg and P. Vermeer, *J. Chem. Soc., Chem. Commun.*, 1983, 1529, all of which disclosures are incorporated in the background herein by reference. The major problem with these compounds heretofore has been their tendency to equilibrate (equation 1) or to react so as to

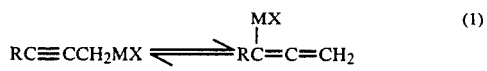

give mixtures of allenic and propargylic products.

The brominaton (pyridinium hydrobromide perbomide), iodination (iodine) and acylation (RCOCl/AlCl$_3$, $-20°$ C., CH$_2$Cl$_2$) of allenic and propargylic organomercurials proceeds with rearrangement to afford higher yields of the corresponding propargylic and allenic bromides, iodides and ketones, respectively.

It has now been found that if one reacts propargylic halides and metallic mercury to provide the corresponding allenic or proparaglic organomercurials, the tendency to equilibrate and to give mixtures of products can be eliminated making the corresponding allenic and propargylic organomercurials highly useful intermediates. This is particularly surprising in view of the teachings of the prior art.

Only one propargylic and one allenic organomercurial are known to have been reported in the literature previously, see M. Gaudemar, *Bull. Soc. Chim. France*, 1962, 974. These compounds were prepared from the corresponding organozinc reagents, thus limiting the types of functional groups which might be accommodated. In 1884, L. Henry, *Ber. Dt. Chem., Ges.*, 1884, 17, 1132 reported that the reaction of propargyl iodide and metallic mercury in sunlight gives propargyl mercuric iodide (eq. 2). This approach to the desired organomercurials

appeared attractive, particularly since it would appear to accommodate a wide range of organic functionality. The reported process of the Henry article has surprisingly been found to be in error. One cannot prepare propargyl mercuric iodide by the process suggested by Henry. Instead, it has surprisingly been found that where a terminal alkyne such as reported by Henry is used in the reaction process in every instance the compound synthesized is an allenic mercurial.

Accordingly, a primary objective of the present invention is to provide a convenient, predictable and selective synthetic route for preparing, at the process operator's wishes, either allenic or propargylic organomercuric halides in high yield.

Yet another objective of the present invention is to prepare, in a single step synthesis reaction, either propargylic or allenic mercuric halides alone, without mixtures of both being present, such that they can selectively be used as synthesis precursors in types of reactions earlier mentioned in the incorporated literature references.

An even further objective of the present invention is to provide a highly convenient route to a variety of allenic and propargylic organomercuric halides in high yields which are readily isolatable for use in further processing reactions.

The method and manner of accomplishing each of the above objectives as well as others will become apparent from the detailed description which will follow hereinafter.

SUMMARY OF THE INVENTION

This invention relates to a method of preparing propargylic and allenic organomercuric halides by reacting a propargylic halide with metallic mercury, in the presence of sunlight. When the halide contains a terminal alkyne it yields an allenic organomercuric halide, and when said halide contains an internal alkyne, it yields a propargylic organomercuric halide if said internal alkyne contains a primary halide, and if said internal alkyne contains a secondary or tertiary halide, it yields an allenic organomercuric halide. The reaction proceeds in high yields and yields exclusively either the propargylic or the allenic organomercuric halide without yielding mixtures of both. Put another way, surprisingly there is no tendency to yield equilibrating mixtures of the two.

DETAILED DESCRIPTION OF THE INVENTION

In accordance with the reaction of the invention, a propargylic halide, preferably a bromide or an iodide is reacted with metallic mercury, preferably in a finely divided state in the presence of sunlight to yield either a propargylic organomercuric halide or an allenic organomercuric halide. The reaction must be conducted in the presence of sunlight or it is found not to go. Put another way, ultraviolet light must be present for the reaction to proceed. The preferred halides are the iodides which are found generally to be somewhat more reactive than the bromides, which are in turn more reactive than the chlorides. Either primary, secondary or tertiary halides may be employed.

The resulting product is either an allenic or a propargylic mercurial, depending on the structure of the starting halide. Terminal alkynes are observed in all cases to afford allenic mercurials. With internal alkynes, primary halides yield propargylic mercurials, while secondary halides, and it is believed tertiary halides afford allenic mercurials. As evidenced from the table below, contrary to the report in the Henry article, the product from propargyl iodide is quite clearly the allenic mercurial and not the propargyl mercurial previously reported. While this is reported in Table 1, the presence of allenic mercurial is confirmed by the presence of a peak at 1926 cm$^{-1}$ (see C=C=C) in the infrared spectrum and NMR spectral peaks at δ4.6 (CH$_2$) and 5.20 (CHHgI).

The reaction can be summarized by the following (equation 2):

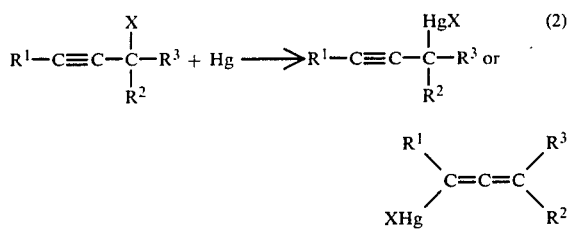

X represents halide.

The reaction does not appear to be either temperature or time dependent. However, preferably the reaction is run at temperatures ranging from 0° C. to room temperature, for from about 0.5 hours to about 4 hours, preferably for from about 1 hour to about 3 hours.

It is desirable that the reaction be run with metallic mercury in a finely divided state in order to allow for easy dispersion of the mercury through the reaction medium. This provides good reactive surface contact. It is also preferred that the reaction be conducted in an inert gas flushed sealed vessel. Suitable inert gases include the commonly available ones, and most preferably nitrogen.

The amount of reactants, that is mercury and the propargylic halide can generally be equimolar or stoichiometric amounts. It has been found desirable, however, to employ excesses of mercury over and above the stoichiometric amount. In particular desirable results seem to be obtained when twice the stoichiometric amount of mercury is employed.

The precise propargylic or allenic halide selected does not appear to be critical and the R$^1$, R$^2$, and R$^3$ moieties of equation 2 are not a limiting factor on the invention, they being capable of being any suitable organic moiety, depending completely upon the ultimate end use reaction in which the prepared propargylic or allenic mercury halide will be employed. Generally, R$^1$, R$^2$, and R$^3$ can be a straight or branched chain C$_1$ to C$_8$ alkyl group, phenyl, C$_1$ to C$_8$ alkenyl and C$_1$ to C$_8$ aralkyl, C$_1$ to C$_8$ referring to the alkyl portion of the aralky. It can also be an alkoxy such as ethoxy, methoxy and the like.

Preferably the reaction is accompanied with agitation of the reaction vessel in order to assure that the memory is finely dispersed.

EXAMPLES

The following examples are shown to further illustrate, but not limit, the process of the present invention.

The general reaction procedure involves mixing 20 mmol of metallic mercury and 10 mmol of the appropriate propargylic halide in a test tube or similar apparatus, flushing with nitrogen before sealing, shaking the tube until the mercury is finely dispersed, and setting the tube in the sunlight for an appropriate amount of time, typically two hours. After storing overnight in the refrigerator, the product is dissolved in tetrahydrofuran or another appropriate recrystallization solvent, the solution filtered, the solvent removed and the resulting crude product recrystallized from a suitable solvent. Confirmation of the presence of the desired product was by infrared spectroscopy, and nuclear magnetic resonance spectroscopy and elemental analysis. While the spectral data is not reported in the table below, the propargylic mercurials were characterized by a lack of allenic hydrogens in the NMR spectra and infrared bands at 2197–2420 cm$^{-1}$ (C C). Corect spectral and elemental analyses were obtained for all compounds (except the unstable compound shown in entry 9). In every instance, as reported in Table 1 below, mixtures of allenic and propargylic mercurials were never observed. These organometallics do not appear to exist in equilibria.

These compounds, that is the produced propargylic and allenic organomercurials, have been found to be quite valuable in organic synthesis and, inter alia, studies are presently occurring for the application of CH$_3$O$_2$C(CH$_2$)$_3$C≡CCH$_2$HgI in prostaglandin synthesis.

TABLE I

Synthesis of Allenic and Propargylic Organomercuric Halides (Examples 1–9)

| Example | Organic Halide | Organomercuric Halide | Recrystallization Solvent(s) | % Isolated Yield |
|---|---|---|---|---|
| 1 | C$_6$H$_5$C≡CCH$_2$Br | C$_6$H$_5$C≡CCH$_2$HgBr | EtOH | 72 |
| 2 | (CH$_3$)$_2$CBrC≡CH | (CH$_3$)$_2$C=C=CHHgBr | THF/acetone | 60 |
| 3 | ICH$_2$C≡CH | H$_2$C=C=CHHgI | ether | 55 |
| 4 | CH$_3$CHIC≡CH | CH$_3$CH=C=CHHgI | THF/ether | 80 |
| 5 | CH$_3$CHIC≡CC$_6$H$_5$ | CH$_3$CH=C=C(C$_6$H$_5$)HgI | THF/ether | 66 |
| 6 | CH$_3$C≡CCH$_2$I | CH$_3$C≡CCH$_2$HgI | THF | 83 |
| 7 | C$_6$H$_5$C≡CCH$_2$I | C$_6$H$_5$C≡CCH$_2$HgI | acteone | 68 |
| 8 | CH$_3$O$_2$C(CH$_2$)$_3$C≡CCH$_2$I | CH$_3$O$_2$C(CH$_2$)$_3$C≡CCH$_2$HgI | THF/ether | 80$^a$ |
| 9 | H$_2$C=C(CH$_3$)C≡CCH$_2$I | H$_2$C=C(CH$_3$)C≡CCH$_2$HgI | — | 72$^b$ |

$^a$Yield based on recovered starting iodide.
$^b$This compound is unstable at room temperature.

In each instance, the general procedure previously described was utilized in preparing the reported compounds, with the only variance being recrystallization solvent as reported.

From the above examples, it can be seen that an important easy-to-run, single-step synthesis has been discovered which is highly predictable and selectively allows one to prepare at one's own will, either propargylic organomercuric halides or allenic organomercuric halides depending upon the starting propargylic halide selected. Moreover, compounds are prepared in high yield not equilibrating mixture, and thus, easily isolatable by recrystallization and available for subsequent use in a variety of organic syntheses including prostaglandin syntheses routes.

What is claimed is:
1. A method of preparing propargylic organomercuric halides, comprising:

reacting a propargylic halide which is an internal alkyne and a primary halide with metallic mercury, in the presence of sunlight to yield the corresponding propargylic organomercuric halide.

2. The method of claim 1 wherein said halide is selected from the group of bromide and iodide.

3. The method of claim 2 wherein said metallic mercury is in a finely divided state to allow easy dispersion through a reaction medium.

4. A method of preparing allenic organomercuric halides, comprising:

reacting a propargylic halide which is an internal alkyne and either a secondary or tertiary halide, with metallic mercury in the presence of sunlight to yield the corresponding allenic mercury halide.

* * * * *